United States Patent [19]

Loewe et al.

[11] Patent Number: 5,718,731
[45] Date of Patent: Feb. 17, 1998

[54] OXIDATION HAIR DYE COMPOSITION BASED ON 4,5-DIAMINOPYRAZOLE AND M-PHENYLENEDIAMINE DERIVATIVES

[75] Inventors: Isolde Loewe, Bensheim; Alexa Weinges, Heidelberg; Wolfgang R. Balzer, Alsbach; Stefan Gerstung, Reinheim, all of Germany

[73] Assignee: Wella Aktiengesellschaft, Darmstadt, Germany

[21] Appl. No.: 696,327

[22] Filed: Aug. 13, 1996

Related U.S. Application Data

[63] Continuation of Ser. No. 491,779, Jun. 19, 1995, abandoned.

[30] Foreign Application Priority Data

Jun. 28, 1994 [DE] Germany ............... 44 22 603.9

[51] Int. Cl.$^6$ ..................................... A61K 7/13
[52] U.S. Cl. .................. 8/409; 8/407; 8/410; 8/411; 8/416; 8/423
[58] Field of Search .................... 8/406, 407, 408, 8/409, 410, 411, 412, 416, 423

[56] References Cited

U.S. PATENT DOCUMENTS

| 3,674,414 | 7/1972 | Kalopissis et al. | 8/11 |
|---|---|---|---|
| 3,712,158 | 1/1973 | Kalopissis et al. | 8/11 |
| 4,092,102 | 5/1978 | Halasz et al. | 8/11 |
| 4,196,145 | 4/1980 | Halasz et al. | 260/573 |
| 5,061,289 | 10/1991 | Clausen et al. | 8/406 |
| 5,380,340 | 1/1995 | Neunhoeffer et al. | 8/423 |
| 5,534,267 | 7/1996 | Neunhoeffer et al. | 8/409 |

FOREIGN PATENT DOCUMENTS

| 0375977 | 7/1990 | European Pat. Off. |
| 1810191 | 11/1968 | Germany. |
| 2160317 | 12/1971 | Germany. |
| 2449101 | 4/1975 | Germany. |
| 208298 | 5/1984 | Germany. |
| 3843892 | 6/1990 | Germany. |
| 4234887 | 4/1994 | Germany. |
| 9408970 | 4/1994 | WIPO. |

OTHER PUBLICATIONS

H. Dorn, et al, Liebigs Ann. Chem. 717, 1968, pp. 118–123.
H. Dorn, et al, Liebigs Ann. Chem. 707, 1967, pp. 141–146.

*Primary Examiner*—Paul Lieberman
*Assistant Examiner*—Caroline Dusheck
*Attorney, Agent, or Firm*—Michael J. Striker

[57] ABSTRACT

The oxidation hair dye composition contains from 0.01 to 4.0 percent by weight of a developer substance including at least one diaminopyrazole of the formula (I)

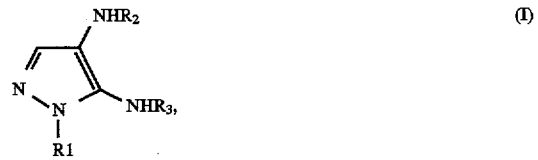

wherein $R^1$ is selected from the group consisting of hydrogen, an alkyl group having from 1 to 6 carbon atoms, a hydroxyalkyl group having from 2 to 4 carbon atoms and a substituted or unsubstituted benzyl group, and $R^2$ and $R^3$, independently, are each selected from the group consisting of hydrogen, an alkyl group having from 1 to 6 carbon atoms and a hydroxyalkyl group having from 2 to 4 carbon atoms; and from 0.01 to 4.0 percent by weight of a coupler substance including at least one m-phenylenediamine selected from the group consisting of N-(3-dimethylamino) phenyl urea and 3-(N-methylsulfonyl)amino-N,N-dimethylaniline.

7 Claims, No Drawings

OXIDATION HAIR DYE COMPOSITION BASED ON 4,5-DIAMINOPYRAZOLE AND M-PHENYLENEDIAMINE DERIVATIVES

This is a continuation of application, Ser. No. 08/491,779, filed under 37 C.F.R. 1.62 on Jun. 19, 1995, now abandoned.

BACKGROUND OF THE INVENTION

The present invention relates to an agent and/or composition for oxidative dyeing of hair based on a combination of developer and coupler substances which contain certain 4,5-diaminopyrazole derivatives as developer substances and certain m-phenylenediamine derivatives as coupler substances.

Oxidation hair dyes have attained considerable importance in the hair dyeing arts. A hair dye mixture is produced by reaction of certain developer substances with certain coupler substances in the presence of a suitable oxidizing agent.

Particularly 2,5-diaminotoluene, 2,5-diaminophenylethyl alcohol, p-aminophenol and 1,4-diaminobenzene are used as developer substances. Resorcinol, 4-chlororesorcinol, 1-naphthol, 3-aminophenol, 5-amino-2-methylphenol and derivatives of m-phenylenediamine are advantageously used as coupler substances.

Oxidation hair dyes which are used for dyeing human hair have numerous special requirements. They must be unobjectionable in toxicological and dermatological respects and they must dye hair so that the desired color intensities are obtained. Furthermore satisfactory light fastness, permanent wave stability, acid fastness and friction fastness are required for the hair color of the hair dyed with the hair dyes. In every case such hair dyes must be stable for time periods of at least 4 to 6 weeks to light, friction and chemical agents. Furthermore a broad palette of different color shades and tones must be available by combination of suitable developer and coupler substances.

Above all p-phenylenediamine derivatives, alone or in a mixture with other developer substances, are used in combination with suitable coupler substances to obtain fashionable color shades or tones in the blue range.

In former times objections regarding physiological compatibility have been raised against the commonly used developer for the blue region of the color palette, p-phenylenediamine, while the more recently recommended developer substances, such as pyrimidine derivatives, are not completely satisfactory in regards to the obtained colors. The pyrazole derivatives described in German patent DE-PS 2 160 317, such as 3-amino-1-phenyl-2-pyrazolone-5, similarly dye hair only with a very much reduced color depth than is acceptable for commercial practice.

The diaminopyrazoles described in German Published Patent Application DE-OS 38 43 892 in combination with the standard couplers produce chiefly an intense red shade with standard coupler substances so that combinations of diaminopyrazoles with other developers of the p-phenylenediamine type must be used.

SUMMARY OF THE INVENTION

It is an object of the present invention to provide an oxidation hair dye composition based on a combination of developer and coupler substances which has very good physiological properties, dyes hair a brilliant blue shade with a comparatively high color depth and especially can be used to produce natural hair colors.

According to the invention the oxidation hair dye compositions which attain the above object in an outstanding way contain a combination of developer and coupler substances, wherein the developer substance comprises at least one diaminopyrazole of the formula (I):

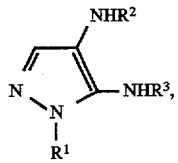

wherein $R^1$ represents hydrogen, an alkyl group having from 1 to 6 carbon atoms, a hydroxyalkyl group having from 2 to 4 carbon atoms or a substituted or unsubstituted benzyl group and $R^2$ and $R^3$ independently represent hydrogen, an alkyl group having 1 to 6 carbon atoms or a hydroxyalkyl group having from 2 to 4 carbon atoms; and the coupler substance comprises m-phenylenediamine of the following formula (II):

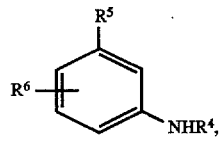

wherein $R^4$ represents $-CONH_2$ or $-SO_2CH_3$; and $R^5$ represents $NR^7R^8$ in which $R^7$ and $R^8$ independently represent hydrogen or an alkyl group having 1 to 4 carbon atoms, and $R^6$ represents hydrogen, an alkoxy-group having 1 to 4 carbon atoms or an alkyl group having 1 to 4 carbon atoms; or their physiologically compatible, water soluble salts.

The 4,5-diamino-1-alkylpyrazoles, 4,5-diamino-1-benzylpyrazole, 4,5-diamino-1-(4'-methylbenzyl)pyrazole and 4,5-diamino-1-(4'-chlorobenzyl)pyrazole are preferred as the developer substance of formula (I) in the oxidation hair dye composition according to the invention. Furthermore N-(3-dimethylamino)phenyl urea and 3-(N-methylsulfonyl)amino-N,N-dimethylaniline are preferred as the coupler substance of formula (II) in the oxidation hair dye composition according to the invention. Both the developer and coupler substance are preferably contained in an amount of about 0.01 to 4.0 percent by weight, advantageously 0.1 to 3.0 percent by weight.

Although the advantageous properties of the developer substances described here permit them to be used alone as the developer substance it is understandably also possible to use the developer substances of formula (I) together with other known developer substances, such as 1,4-diaminobenzene, 2,5-diaminotoluene or 2,5-diaminophenylethanol.

Similarly it is also possible to use other conventional coupler substances in addition to the coupler substance of formula (II) in the oxidation hair dye compositions according to the invention. For example conventional coupler substances which can be used together with the coupler substance of formula (II) include resorcinol, 4-chlororesorcinol, 4,6-dichlororesorcinol, 2-methylresorcinol, 2-amino-4-(2'-hydroxyethyl) aminoanisole, m-phenylenediamine, 5-amino-2-methylphenol, 2,4-diaminophenoxyethanol, 4-amino-2-hydroxyphenoxyethanol, 1-naphthol, 3-aminophenol, 3-amino-2-methylphenol, 4-hydroxy-1,2-methylenedioxybenzene, 4-amino-1,2-methylenedioxybenzene, 2,4-diamino-5-methylphenetole, 4-hydroxyindole and 3,5-diamino-2,6-dimethoxypyridine.

The coupler substance and the developer substance can be included in the oxidation hair dye composition alone or in a mixture with each other.

The total amount of the developer-coupler substance combination contained in the hair dye composition described here amounts to from 0.02 to 8.0 percent by weight, while from 0.2 to 6.0 percent by weight is particularly preferred.

The developer components are generally present in the hair dye composition in approximately equimolar amounts relative to the coupler components. However there is no disadvantage to using a certain excess of developer components relative to coupler components or of coupler components relative to developer components.

The oxidation hair dye composition according to the invention can also contain other additional hair dye components, for example 6-amino-2-methylphenol or 2-amino-5-methylphenol, as well as additional conventional direct hair dyes, for example triphenylmethane dye compounds such as 4-[4'-aminophenyl)-(4"-imino-2",5"-cyclohexadien-1"-yliden)methyl]-2-methylaminobenzene monohydrochloride (C.I. 42 510) and 4-[4'-amino-3'-methylphenyl)-(4"-imino-3"-methyl-2",5"-cyclohexadien-1"-yliden)methyl]-2-methylaminobenzene monohydrochloride (C.I. 42 520), aromatic nitro dye compounds such as 2-amino-4,6-dinitrophenol, 2-amino-5-(2'-hydroxyethyl)aminonitrobenzene and 2-methylamino-5-bis-(2'-hydroxyethyl)aminonitrobenzene, azo dye compounds such as 7-[4'-aminophenyl)azo]-8-hydroxynaphthalin-4-sulfonic acid sodium salt (C.I. 14 805) and dispersion dye compounds such as 1,4-diaminoanthraquinone and 1,4,5,8-tetraaminoanthraquinone. The oxidation hair dye composition according to the invention can contain these hair dye compounds in amounts of from about 0.1 to 4.0 percent by weight.

Understandably the coupler and developer substances and the other dye compounds or components, in so far as they are bases, can be used in the form of physiologically compatible salts with organic or inorganic acids, for example sulfuric and hydrochloric acid, and, in so far as they have aromatic OH groups, in the form of salts with bases, e.g. as alkali metal phenolates.

Furthermore additional conventional cosmetic additives may be present in the oxidation hair dye compositions according to the invention. These additional conventional cosmetic additives include, for example, antioxidants such as ascorbic acid, thioglycolic acid or sodium sulfite; perfume oils; complex formers; wetting agents and emulsifiers; thickeners and hair care compounds.

The oxidation hair dye compositions can be in the form of a solution, especially an aqueous or aqueous-alcoholic solution. However they can also be in the form of a cream, a gel or an emulsion.

The oxidation hair dye compositions of the invention comprise a mixture of the hair dye components with the additional cosmetic additives which are suitable in this type of composition.

The additional cosmetic additives can be provided in solutions, creams, emulsions or gels and include, solvents, e.g. water and lower aliphatic alcohols such as ethanol, propanol, isopropanol and glycerin; or glycols, e.g. 1,2-propyleneglycol; additional wetting agents and emulsifiers from the classes of anionic, cationic, amphoteric or nonionic surface active substances, such as fatty alcohol sulfates, ethoxylated fatty alcohol sulfates, alkylsulfonates, alkylbenzenesulfonates, alkyltrimethylammonium salts, alkylbetaine, ethoxylated fatty alcohols, ethoxylated nonylphenol, fatty acid alkanolamides, ethoxylated fatty acid esters; thickeners such as higher fatty alcohols, starches, cellulose derivatives, vaseline, paraffin oils and fatty acids as well as additional hair care materials such as cationic resins, lanolin derivatives, cholesterol, pantothenic acid and betaine. The above mentioned cosmetic additives should be used in amounts which are effective and suitable for their purposes, e.g. the wetting agents and emulsifiers are used in concentrations of about 0.5 to 30 percent by weight, the thickeners in amounts of from about 0.1 to 25 percent by weight and the hair care components in concentrations of from about 0.1 to 5.0 percent by weight.

The oxidation hair dye composition can be weakly acidic, neutral or alkaline according to its composition. Particularly it has a pH value of 6.5 to 11.5, which can be adjusted, for example, with ammonia. However also an organic amine, e.g. monoethanolamine and triethanolamine, or also an inorganic base such as sodium hydroxide and potassium hydroxide can be used.

In practice for oxidative dyeing of hair the above-described oxidation hair dye composition is generally mixed with an oxidizing agent immediately prior to use and the mixture is then applied in an amount sufficient for dyeing of hair to the hair according to the amount of hair present, generally in an amount of about 60 to 200 grams.

Hydrogen peroxide or its addition compounds with urea, melamine or sodium borate are used as oxidizing agent for developing the hair color of the dyed hair in the form of a 3- to 12-percent, advantageously 3- to 6- percent, aqueous solution, but atmospheric oxygen can also be used. If a 4- to 6-percent hydrogen peroxide solution is used as oxidizing agent, the weight ratio of hair dye composition to oxidizing agent is advantageously 5:1 to 1:2, but a 1:1 weight ratio is particularly preferred. Larger amounts of oxidizing agent are, above all, used with greater dye concentration in the oxidation hair dye composition or when simultaneously a stronger bleaching of the hair is intended. The mixture of oxidation hair dye composition and oxidizing agent is allowed to act on the hair for about 10 to 45 minutes, advantageously 30 minutes, at temperatures of from 15° to 50° C. Then the hair is rinsed with water and dried. In connection with the rinsing the hair can be washed with a shampoo as needed and eventually with a weak organic acid, such a citric acid or tartaric acid. Subsequently the hair is dried.

The developer substances of formula (I) and the coupler substances of formula (II) should be used in the oxidation hair dye composition either in the free base form or in their physiologically compatible salt form. The physiologically compatible salts can be formed by reacting the free base form with inorganic or organic acids, e.g. hydrochloric acid, sulfuric acid, phosphoric acid, acetic acid, propionic acid, lactic acid or citric acid. The compounds of formula (I) and (II) are sufficiently soluble in water and they have also an outstanding storage stability, particularly as component of the hair dye composition described here.

The hair dye compositions according to the invention allow the production of fashionable blue shades or tones with extraordinarily greater color depth and comparatively higher stability. The very good color properties of the hair dye compositions according to the present invention have also been shown to provide a problem-free dyeing of gray, not previously damaged hair with good color coverage.

The manufacture of coupler substance according to the invention can proceed analogously to the manufacturing processes described in German Published Patent Application DE-OS 24 49 101 and German Patent DE-PS 1 810 191.

Accordingly the urea derivative of the general formula (II) can be produced by reacting the aniline derivative with potassium isocyanate, while the methyl sulfonamide derivatives of formula (II) are obtained by reacting 3-nitroaniline with methanesulfonic acid chloride and subsequent reduction.

The methods for making the developer substances of formula (I) for the oxidation hair dye compositions according to the invention are described in the Literature, for example in German Published Patent Application DE-OS 3 843 892 and H. Dorn et al, Liebigs Annalen der Chemie 707(1967), pp. 141 to 146 and H. Dorn et al, Liebigs Annalen der Chemie 717(1968), pp. 118 to 123.

The preparation of a substituted 4,5-diamino-1-benzylpyrazole with a substituent on the benzene ring is possible in a comparatively simple manner by reaction of 3,5-dibromo-4-nitropyrazole (III) with the appropriate substituted benzylhalide according to the following reaction scheme in accordance with the method described in German Published Patent Application DE-OS 42 34 887.

advantageously with R=H, halogen; alkyl groups with one to six carbon atoms, hydroxyalkyl groups with one to six carbon atoms; dihydroxyalkyl with two to six carbon atoms; alkoxy groups with one to six carbon atoms; hydroxy groups; cyano groups; monohydroxy-$(C_1-C_4)$alkylamino groups; dihydroxy-$(C_1-C_4)$alkylamino groups; amino groups; $C_1-C_6$-monoalkylamino groups; and $C_1-C_6$-dialkylamino groups.

The following examples should illustrate the invention without limiting the claims appended here below.

PRODUCTION EXAMPLES

Example 1

Synthesis of 1-benzyl-3,5-dibromo-4-nitropyrazole (IV)

General Instructions

To 1.75 g (70 mmol) sodium hydride (96%) in 150 ml absolute dimethylformamide (DMF) 19.0 g (70 mmol) of 3,5-dibromo-4-nitropyrazole are added dropwise over a time interval of one hour. Copious gas evolution and heating of the reaction solution occurs. As soon as gas has been generated, the solution appears a clear orange color. Now 30 ml of DMF containing 70 mmol of benzyl halide is added dropwise and the resulting solution is heated for 3 hours at 80° C. The solvent is distilled away in vacuo and the residue is recrystallized from methylene chloride.

I. 3,5-dibromo-1-(4'-methylbenzyl)-4-nitropyrazole 9.8 g (70 mmol) 4-methyl-benzylchloride are reacted according to the above-described general prescription.

Yield:

18 g (68 percent of theoretical) 3,5-dibromo-1-(4'-methylbenzyl)-4-nitropyrazole are formed and have a melting point of 108° C. This product had the following NMR and mass spectra.

$^1$H-NMR (300 MHz, DMSO-$d_6$): σ=2.28 ppm (s; 3H; —CH$_3$); 5.45 ppm (s; 2H; —CH$_2$—); 7.18 ppm (m; 4H; $C_6H_5$—H). MS (70 eV): m/e=375 (M$^{+\cdot}$)

II. 3,5-dibromo-1-(4'-chlorobenzyl)-4-nitropyrazole 11.3 g (70 mmol) of 4-chlorobenzylchloride are reacted according with the above-described instructions.

Yield:

25 g (91 percent of theoretical ) of 3,5-dibromo-1-(4'-chlorobenzyl)-4-nitropyrazole are formed and have a melting point of 109° C. and the following NMR and mass spectra:

$^1$H-NMR (300 MHz, DMSO-$d_6$): σ=5.51 ppm (s; 2H; —CH$_2$); 7.28 ppm (d; J=8.4 Hz; 2H; $C_6H_5$—3H and $C_6H_5$—5H); 7.75 ppm (d; J=8.4 Hz; 2H; $C_6H_5$—2H and $C_6H_5$—6H). MS (70 eV): m/e=395 (M$^{+\cdot}$)

Example 2

Synthesis of 5-benzylamino-1-benzyl-3-bromo-4-nitropyrazole (V)

I. 5-benzylamino-3-bromo-1-(4'-methylbenzyl)-4-nitropyrazole (V)

15 g (40 mmol) of 3,5-dibromo-1-(4'-methylbenzyl)-4-nitropyrazole are mixed with 15 ml benzylamine in 120 ml of ethanol. After one hour heating the reaction mixture is poured into ice, filtered with suction and the product is recrystallized from ethanol.

Yield:

10.0 g (62% of theoretical yield) of 5-benzylamino3-bromo-1-(4'-methylbenzyl)-4-nitropyrazole are formed and have a melting point of 108° C. and the following NMR and mass spectra:

$^1$H-NMR (300 MHz, DMSO-$d_6$): σ=2.29 ppm (s; 3H; —CH$_3$); 4.54 ppm (d; J=6.4 Hz; 2H; NH—CH$_2$—; after D$_2$O exchange s); 5.51 ppm (s; 2H; 1—CH$_2$); 7.15–7.35 ppm (m; 9H; $C_6H_5$—H); 8.00 ppm (t; J=6.4 Hz; 1H; NH; exchange with D$_2$O) MS (70 eV): m/e=400 (M$^{+\cdot}$)

II. 5-Benzylamino-3-bromo-1-(4'-chlorobenzyl)-4-nitropyrazole 9.88 g (25 mmol) 3,5-dibromo-1-(4'-chlorobenzyl)-4-nitropyrazole are heated in 50 ml of ethanol with 15 ml benzylamine for one hour. The resultant mixture is poured into ice, filtered with suction and crystallized from ethanol.

Yield:

8 g (76 percent of theoretical) 5-benzylamino-3-bromo-1-(4'-chlorobenzyl)-4-nitropyrazole are formed and have a melting point of 139° to 141° C. and the following NMR and mass spectra:

$^1$H-NMR (300 MHz, DMSO-d$_6$): σ=4.54 ppm (d; J=5.4 Hz; 2H; NH—CH$_2$—; s after D$_2$O exchange); 5.23 ppm (s; 2H; 1—CH$_2$); 7.10–7.38 ppm (m; 9H; C$_6$H$_5$—H); 8.00 ppm (t; 1H; NH; exchange with D$_2$O).

Example 3

Synthesis of 1-Benzyl-4,5-diaminopyrazole of the Formula (VI)

General Instructions: Hydrogenation of 5-benzylamino-1-benzyl-3-bromo-4-nitropyrazole (V)

The given amount of 5-benzylamino-1-benzyl-3-bromo-4-nitropyrazole (V) is introduced with 130 ml ethanol and 2 spatula tip amounts of a palladium/activated charcoal catalyst (10%) into an autoclave (250 ml) and during the given time interval is stirred in a 50 bar hydrogen atmosphere and at room temperature. After the end of the reaction the resultant mixture is transferred by suction with a water-jet pump into a glass flask and is immediately filtered through a glass frit. The filtrate is mixed with an equimolar amount of 97% sulfuric acid.

I. 4,5-diamino-1-(4'-methylbenzyl)pyrazole 3.0 g (7.5 mmol) of 5-benzylamino-3-bromo-1-(4'-methylbenzyl)-4-nitropyrazole are hydrogenated 4 hours according to the above-described instructions. One obtains 1.90 g (84 percent of theoretical) of 4,5-diamino-1-(4'-methylbenzyl)pyrazole hydrosulfate with a melting point of 163° to 167° C. (with decomposition) and the following NMR and mass spectra:

$^1$H-NMR (300 MHz, DMSO-d$_6$): σ=2.26 ppm (s; 3H; —CH$_3$); 5.12 ppm (s; 2H; —CH$_2$); 5.8–6.7 ppm (s; br; 6H; NH$_2$; H$_2$SO$_4$; exchange with D$_2$O); 7.05–7.21 ppm (m; 4H; C$_6$H$_5$—H); 7.31 ppm (s; 1H; 3—H). MS (70 eV): m/e=202 (M$^+$)

II. 4,5-diamino-1-(4'-chlorobenzyl)pyrazole 3.15 (7.5 mmol) 5-benzylamino-3-bromo-1-(4'-chlorobenzyl)-4-nitropyrazole was hydrogenated 3 hours according to the above-described instructions. 2 g (82% of theoretical yield) of 4,5-diamino-1-(4'-chlorobenzyl) pyrazole hydrosulfate are formed having a melting point of 188° C. (with decomposition) and the following NMR and mass spectra.

$^1$H-NMR (300 MHz, DMSO-d$_6$): σ=5.12 ppm (s; 2H; —CH$_2$); 6.0–6.8 ppm (s; br; 6H; NH$_2$; H$_2$SO$_4$; exchange with D$_2$O); 7.13–7.39 ppm (m; 5H; 3—H and C$_6$H$_5$—H). MS (70 eV): m/e=222 (M$^+$)

For all $^1$H-NMR spectra: s=singlet; d=doublet; t=triplet; m=multiplet; br=broad signal.

OXIDATION HAIR DYE COMPOSITION EXAMPLES

Examples 4 to 8

Hair Dye Compositions 0.025 mol developer according to Table I
0.025 mol coupler according to Table I
10.00 g lauryl alcohol diglycolether sulfate sodium salt (28% aqueous solution)
10.00 g ammonia (22% by weight aqueous solution)
plus added water—until the total amount of the composition equals
100.000 g Immediately prior to use 50 g of the above-described hair dye composition example is mixed with 50 g of a 6% by weight hydrogen peroxide solution and this mixture acts for 30 minutes at 40° C. on blond natural hair. The hair is then rinsed with water and dried. The resultant colors of the dyed hair are tabulated in Table I.

Unless otherwise stated all percentages are by weight.

TABLE I

DYED HAIR COLORS OBTAINED WITH VARIOUS DEVELOPER COUPLER COMBINATIONB

| Example | Developer | Coupler | Color |
|---|---|---|---|
| 4 | 4,5-diamino-1-isopropylpyrazole | N-[(3-dimethylamino)-phenyl]urea | Blue |
| 5 | 4,5-diamino-1-isopropylpyrazole | N-(3-amino-4-methoxy-phenyl)urea | Dark Violet |
| 6 | 4,5-diamino-1-(4'-methylbenzyl)pyrazole | 3-(N-methylsulfonyl-amino)-N,N-dimethyl-aniline | Blue |
| 7 | 4,5-diamino-1-(4'-methylbenzyl)pyrazole | N-(3-amino-4-methyl-phenyl)urea | Violet |
| 8 | 4,5-diamino-1-(4'-chlorobenzyl)pyrazole | 2-amino-4-(N-methyl-sulfonyl)amino anisole | Bright Violet |

While the invention has been illustrated and described as embodied in oxidative hair dye compositions based on 4,5-diaminopyrazoles and m-phenyldiamine derivatives, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. An oxidation hair dye composition containing from 0.01 to 4.0 percent by weight of a developer substance comprising at least one diaminopyrazole of the formula (I)

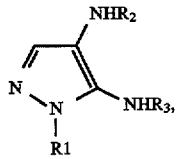

wherein R$^1$ is selected from the group consisting of hydrogen, an alkyl group having from 1 to 6 carbon atoms, a hydroxyalkyl group having from 2 to 4 carbon atoms and a substituted or unsubstituted benzyl group, and R$^2$ and R$^3$, independently, are each selected from the group consisting of hydrogen, an alkyl group having from 1 to 6 carbon atoms and a hydroxyalkyl group having from 2 to 4 carbon atoms; and from 0.01 to 4.0 percent by weight of a coupler substance comprising at least one m-phenylenediamine selected from the group consisting of N-(3-dimethylamino) phenyl urea and 3-(N-methylsulfonyl)amino-N,N-dimethylaniline.

2. An oxidation hair dye composition as defined in claim 1, wherein said at least one diaminopyrazole is selected from the group consisting of 4,5-diamino-1-alkylpyrazoles, 4,5-diamino-1-benzylpyrazole, 4,5-diamino-1-(4'-methylbenzyl)pyrazole and 4,5-diamino-1-(4'-chlorobenzyl) pyrazole.

3. An oxidation hair dye composition as defined in claim 1, further comprising a hair dye component selected from the group consisting of 6-amino-2-methylphenol, 2-amino-5-methylphenol, 4-[4'-aminophenyl)-(4"-imino-2",5"-cyclohexadien-1"-yliden)methyl]-2-methylaminobenzene monohydrochloride, 4-[4'-amino-3'-methylphenyl)-(4"-imino-3"-methyl-2",5"-cyclohexadien-1"-yliden)methyl]-2-methylaminobenzene monohydrochloride, 2-amino-4,6-dinitrophenol, 2-amino-5-(2'-hydroxyethyl)aminonitrobenzene, 2-methylamino-5-bis-(2'-hydroxyethyl)aminonitrobenzene, 7-[4'-aminophenyl)azo]-8-hydroxynaphthalen-4-sulfonic acid sodium salt, 1,4-diaminoanthraquinone and 1,4,5,8-tetraaminoanthraquinone.

4. An oxidation hair dye composition as defined in claim 1, wherein said developer substance also includes at least one member selected from the group consisting of 1,4-diaminobenzene, 2,5-diaminotoluene and 2,5-diaminophenylethanol.

5. An oxidation hair dye composition as defined in claim 1, wherein said coupler substance also includes at least one member selected from the group consisting of resorcinol, 4-chlororesorcinol, 4,6-dichlororesorcinol, 2-methylresorcinol, 2-amino-4-(2'-hydroxyethyl)aminoanisole, m-phenylenediamine, 5-amino-2-methylphenol, 2,4-diaminophenoxyethanol, 4-amino-2-hydroxyphenoxyethanol, 1-naphthol, 3-aminophenol, 3-amino-2-methylphenol, 4-hydroxy-1,2-methylenedioxybenzene, 4-amino-1,2-methylenedioxybenzene, 2,4-diamino-5-methylphenetole, 4-hydroxyindole and 3,5-diamino-2,6-dimethoxypyridine.

6. An oxidation hair dye composition as defined in claim 1, having a pH from 6.5 to 11.5.

7. An oxidation hair dye composition as defined in claim 1, in a the form of an aqueous or aqueous-alcoholic solution, a cream, gel or an emulsion.

* * * * *